United States Patent

Quinlan

[11] 4,113,709
[45] Sep. 12, 1978

[54] POLYQUATERNARY POLYTHIAZINES

[75] Inventor: Patrick M. Quinlan, Webster Groves, Mo.

[73] Assignee: Petrolite Corporation, St. Louis, Mo.

[21] Appl. No.: 713,666

[22] Filed: Aug. 12, 1976

[51] Int. Cl.$^2$ .............................................. C08G 75/24
[52] U.S. Cl. ...................................... 424/78; 8/115.6;
106/15 R; 210/500 R; 424/246; 526/21;
526/36; 528/377; 544/58; 544/60; 544/59
[58] Field of Search ................. 260/79.3 M, 79.3 MU,
260/DIG. 17, 243 R, 243 B; 210/500 R;
8/115.6; 106/15 R; 424/246

[56] References Cited

U.S. PATENT DOCUMENTS

| 2,675,381 | 4/1954 | Craig et al. ........................ 260/243 B |
| 2,752,343 | 6/1956 | Fegley et al. ..................... 260/243 B |
| 3,017,416 | 1/1962 | Lo et al. .......................... 260/243 B |
| 3,055,939 | 9/1962 | Cavallito et al. ................ 260/243 B |
| 3,409,626 | 11/1968 | Cavallito et al. ................ 260/243 B |
| 3,828,036 | 8/1974 | Quinlan ........................... 260/243 R |
| 4,009,201 | 2/1977 | Steckler et al. ................. 260/243 B |

*Primary Examiner*—Ronald W. Griffin
*Attorney, Agent, or Firm*—Sidney B. Ring; Hyman F. Glass

[57] ABSTRACT

This invention relates to polymers of quaternary thiazines having the recurrent structure

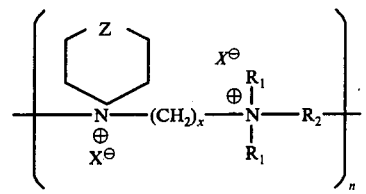

where Z is S, SO, SO$_2$, x is 2 or more, R$_1$ is a hydrocarbon or substituted hydrocarbon, R$_2$ is alkylene, alkenylene, aralkylene, alkylene ether, X is an anion, n is a number from 3–500. These polymers are useful as flocculants and/or water clarifiers, corrosion inhibitors, antistatic agents, demulsifiers, microbiocides, algicides and the like.

17 Claims, No Drawings

POLYQUATERNARY POLYTHIAZINES

In Application Ser. No. 713,706 filed Aug. 12, 1976 there are described and claimed tertiary amino-substituted thiazines. This Application Ser. No. 713,706 is by reference incorporated into the present application as if part hereof.

Ser. No. 713,706 relates to tertiary amino-substituted thiazines such as 4-(tertiaryaminoalkylene) substituted 1,4-thiazines of the formulae:

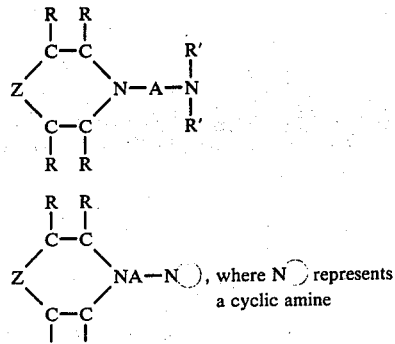

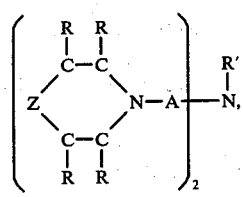, where N represents a cyclic amine

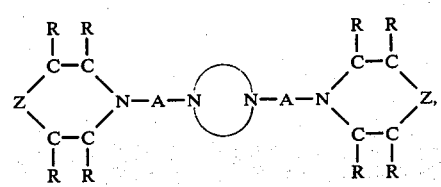

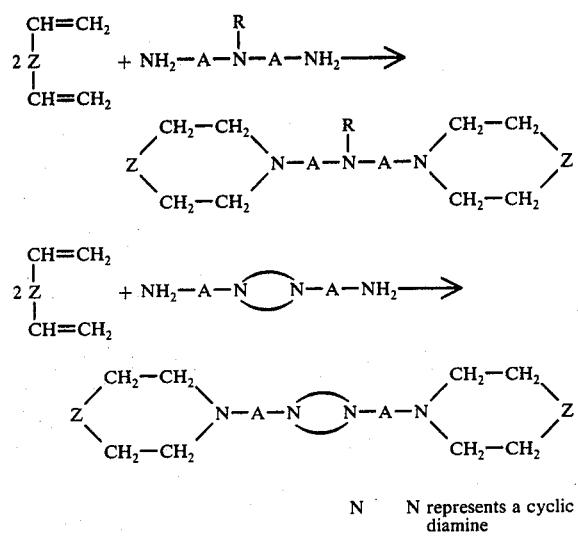

where N ⌣ N represents a cyclic diamine group.

where the R's are hydrogen or a substituted group such as a hydrocarbon group, i.e., alkyl, etc.; and R' is a hydrocarbon group such as alkyl, or a substituted alkyl such as hydroxyalkyl and the like; Z is S, SO, $SO_2$; and A is alkylene, alkenylene, alkinylene, etc.

When divinyl sulfone is treated with a primary amine, derivatives of 1,4-thiazine-1,1-dioxide result. The compounds of this invention are prepared by reacting a divinyl sulfur compound with an organic compound containing one or more primary and tertiary amino groups. The reaction of a compound containing one primary and one tertiary amino group such as N,N dimethyl-1,3-propanediamine may be illustrated by the following general equation:

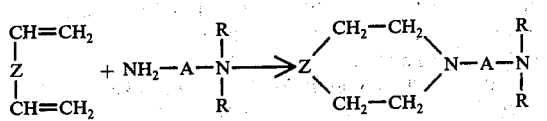

where A is alkylene such as $(CH_2)_{2-10\ or\ greater}$ and the R's are hydrocarbon such as alkyl, substituted alkyl, etc.

In addition one mol of an alkylimino bis-alkylamine having two primary amino groups and one tertiary amino group such as methyliminobispropylamine or an N,N'-bis (aminoalkylene)-di-tertiary amine such as N,N'bis(3-aminopropyl)-piperazine having two primary amino groups and two tertiary amino groups reacts with two mols of a divinyl sulfur compound in a similar manner.

The amine which reacts with the divinyl sulfur compound contains at least one primary amino group and at least one tertiary amino group. Thus, it may contain one primary and one tertiary amino group, e.g., $$NH_2A—N=$$

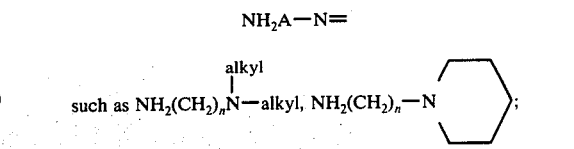

$n = 2-10$ or greater one tertiary amino group and two primary amino groups such as

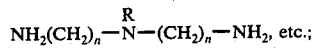

two tertiary and two primary amino groups such as

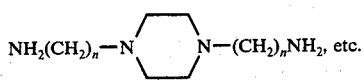

In the resulting product the primary amino group or groups become part of the thiazine ring while the tertiary amino group remains unchanged. Thus, the final product contains one or two thiazine groups and one or two tertiary amino groups.

Examples of the divinyl sulfur compounds are:

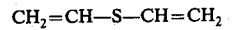
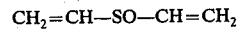
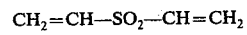

Examples of compounds having one priamry amino group and one tertiary amino group include N,N-dimethyl propanediamine, N,N-diethylpropanediamine, N,N-diethylethylenediamine, N-(3-aminopropyl) diethanolamine, N-(3-piperidino) propylamine, N-(3-aminopropyl9 morpholine and the like.

An example of a compound having two primary amino groups and two tertiary amino groups is N,N'-Bis(3-aminopropyl)piperazine.

In carrying out the reaction the divinyl sulfone is usually added to an alcoholic solution of the amine. However any non-reactive solvent may be employed. In some cases the amine is added to an alcoholic solution of the divinyl sulfone particularly when a plurality of primary amino groups is present. The reaction is exothermic and cooling is usually employed to moderate the heat of reaction. A reaction temperature of between 25° and 60° C is preferred. After addition a short period of reflux may be employed to ensure complete reaction. The reaction product may be isolated and purified by employing conventional techniques. The yields of the desired products are quite excellent.

The invention may be illustrated by the following examples.

EXAMPLE 1

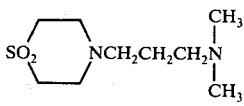

To 102g. (1 mol) of N,N-dimethyl 1,3-propanediamine dissolved in 150 ml. of methanol was slowly added, with external cooling, 118g. (1 mole) of divinyl sulfone. After the addition had been completed, the mixture was heated at reflux for 1 hour. The methanol was stripped off, using a rotary evaporator, leaving a viscous liquid product. The product was distilled in vacuo. The main portion had a B.P. of 170–172/2mm. Recovered 176g. of a yellow viscous liquid (80% of theory)

Analyses - Calculated For $C_9H_{20}N_2O_2S$(percent): N, 12.75; S, 14.54 Found (percent): N, 12.78; S, 14.37.

IR and NMR spectra were used to characterize and verify the above structure.

EXAMPLE 2

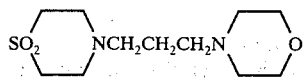

118g. (1 mol) of divinylsulfone was added with cooling to a solution of 144.2g. (1 mol) of N-aminopropyl morpholine in 350 ml. of methanol. After the addition had been completed, the solution was heated at reflux for 1 hr. Methanol was removed leaving a viscous liquid that crystallized upon standing. The crude product was recrystallized from ethanol.

Analyses: - Calculated for $C_{11}H_{22}N_2O_3S$: N, 10.69, S, 12.21. Found: N, 10.46; S, 11.86.

EXAMPLE 3

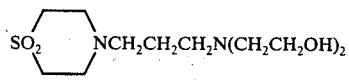

162g. (1 mol) of N-(3-aminopropyl) diethanolamine was dissolved in 300 ml. of methanol. To this solution was slowly added with cooling 118g. (1 mol) of divinyl sulfone. The crude product was isolated and purified by distillation.

EXAMPLE 4

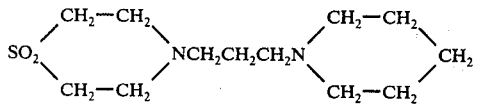

To 12.8g. (0.1 mol) of 3-(N-piperidino)propylamine in 50 ml. of ethanol as added with cooling 11.8g. (0.1 mol) of divinylsulfone. After the addition was completed the reaction mixture was heated at reflux for 1 hr. The product was stripped of ethanol and isolated by distillation. The structure was characterized by NMR and IR spectra.

EXAMPLE 5

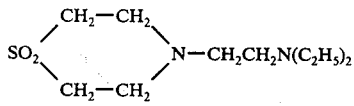

To 116g. (1 mol) of N,N-diethyl ethylenediamine in 350 ml. of methanol was added with cooling 118g. (1 mol) of divinylsulfone. After the addition was completed the reaction mixture was heated at reflux for 1 hr. The product was stripped of methanol and isolated by distillation.

EXAMPLE 6

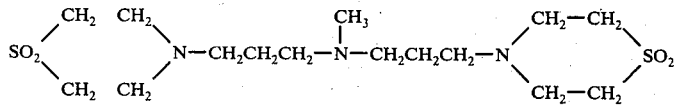

To 236.05g. (2 mol) of divinylsulfone dissolved in 350 ml. of 2-propanol was slowly added with cooling 145.0g. (1 mol) of methyliminobispropylamine. After the addition had been completed, the reaction mixture was heated at reflux for 1 hour. The 2-propanol was removed on a rotary evaporator and the crude liquid product crystallized upon standing. It was recrystallized from ethanol.

Analyses: - Calculated for $C_{15}H_{31}N_3O_4S_2$: N, 9.07; S, 16.80. Found - N, 9.00; S, 16.72

The above structure was characterized by NMR and IR spectra.

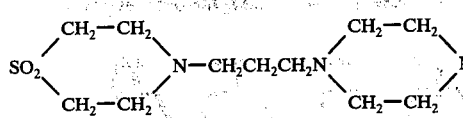 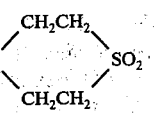

To 100g. (0.5 mol) of N,N'-Bis(3-aminopropyl) piperazine dissolved in 200 ml. of 2-propanol was slowly added with cooling 118g. (1 mol) of divinylsulfone. After the addition had been completed, the reaction mixture was heated at reflux for 1 hr. The 2-propanol was removed using a rotary evaporator leaving a white powder. The solid was purified by washing with acetone and recrystallized from a mixture of benzene and petroleum ether.

Analyses - Calculated for $C_{18}H_{36}N_4O_4S_2$;
N, 12.84; S, 14.68. Found - N, 12.74; S, 14.73.

I have now discovered that the tertiary amino-substituted thiazines can be converted to polyquaternary polythiazines by reacting the tertiary amino-substituted thiazines with alkylating-type difunctional compounds such as dihalides or their equivalents. By alkylating-type difunctional compounds I mean hydrocarbon or related groups containing at least one reactive moiety such as a halide which reacts with an amino group to form a quaternary ammonium group while the functional moiety such as the halide forms the anion moiety of the quaternary.

More particularly, this invention pertains to polyquaternary polythiazines having the following structure:

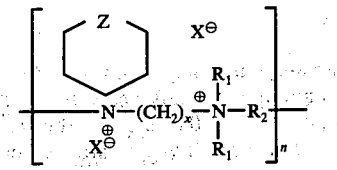

where Z is S, SO, $SO_2$. x is 2 or greater but preferably 3 or greater, $R_1$ is a hydrocarbon or a substituted hydrocarbon, for example alkyl, hydroxyalkyl, etc. $R_2$ is alkylene, alkenylene, alkylarylene, alkylene ether, etc., X is an anion. n is a number such as from 3-500, such as from 10-250, but preferably from 30-100.

The products are useful as fluocculants and/or water clarifiers, corrosion inhibitors, antistatic agents, demulsifiers, microbiocides, algicides, and the like.

When compounds of the type

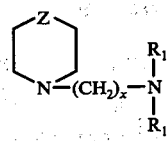

are reacted, in about a 1:1 molar ratio with bis-halide compounds in a suitable solvent or solvent mixtures at room temperature, polyquaternary compounds are formed. To illustrate the reaction the following general equation is shown:

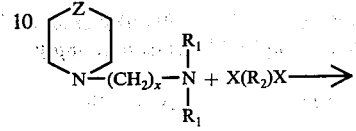

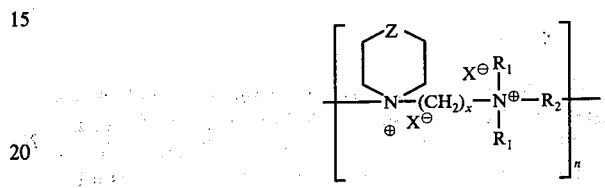

The synthesis of a variety of polyquaternary polythiazines with yields of over 90% can be achieved at room temperature in a number of solvents, e.g., dimethyl sulfoxide, methanol, benzene, dimethylformamide (DMF), dimethyformamide — water mixtures, and various combinations of above. The reaction rates are greatly solvent-dependent, i.e., the higher the dielectric constant of the medium the higher the rate. The rate of formation of a polyquaternary ammonium chloride is considerably smaller than that of a corresponding bromide.

The reaction is normally carried out at room temperature; that is about 25° C. Higher temperatures such as 75° C may be employed. This leads to a much faster rate of reaction; however the specific viscosity of the corresponding polymer solution is much smaller than that obtained at 25° C using the same reactants and solvent medium. Therefore the preferred reaction temperature is from 20°-30° C.

The reaction time at room temperature may vary from about 5 hours up to a period of one month. However the normal reaction time is from 48 hours to about 720 hours. The preferred reaction time at room temperature is from 96 to 600 hours.

It was found that the polymers obtained at high reagent concentration had a higher specific viscosity than those prepared in dilute solutions. The concentration of reactants may vary from 0.1 moles/liter to 2.5 moles/liter. However the preferred concentration is from 0.5 moles/liter to 1.0 moles/liter.

The usual and preferred methods of preparation of the polyquaternary compounds of this invention is as follows. A solution of the ditertiary amine compound was mixed thoroughly with a solution of the dihalide compound and the mixture was left at room temperature (22° C). The molar ratio of the diamine to the dihalide was in all cases about 1:1. After a given time, the precipitated polymer was filtered; washed quickly with a small amount of the solvent, then with benzene, and finally with acetone; and dried under high vacuum at 40° C. The filtrate was poured into a large excess of acetone with stirring. The precipitated polymer was filtered, washed first with benzene and then with acetone, and dried as before. All of the polymers prepared were found to be soluble in water with varying degrees of solubility in methanol and insoluble in common organic solvents. They may be isolated, as described above, or diluted with water and used.

All viscosity measurements were made by diluting the polymers in distilled water to the desired concentration ($2 \times 10^{-3}$M). An Ostwald Viscometer, in a bath at 25° C ± 0.1° C, was used to measure the specific viscosities.

$X-R_2-X$ may be a wide variety of polymerizing compounds, i.e., capable of joining amino groups, where $R_2$ may be alkylene, alkenylene, alkynylene, alkaralkylene, an alkyleneether-containing group, an ester-containing group, etc., and X is a halide.

The following are non-limiting examples: (I) Saturated dihalides

where $R_2$ is alkylene, straight chain or branched, for example $X(CH_2)_nX$ where n is 3–25 or more, for example 3–10, but preferably 3–6. The $+CH_2 \rightarrow_n$ may be branched such as where at least one of the H's is a hydrocarbon group such as alkyl, i.e., methyl, ethyl, etc., substituted such as halo, hydroxy, etc. (II) Aralkylene dihalides

where $R_2$ is aralkylene having for example 8–30 or more carbons, such as 8–20 carbons, but preferably xylylene.

The following are illustrative examples:

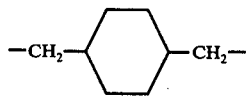

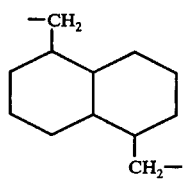

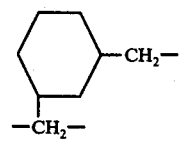

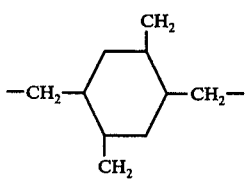

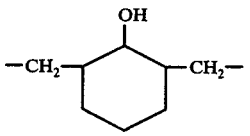

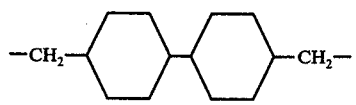

Additional examples of aralkylene radicals include those of the formula $-CH_2-Ar-CH_2-$ where Ar is

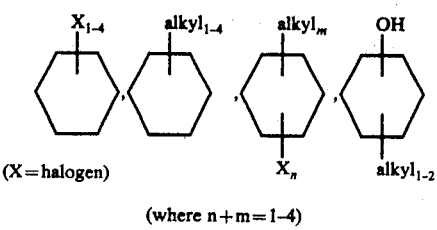

(X=halogen)

(where n+m=1–4)

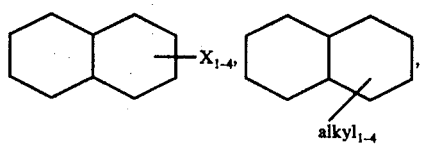

alkyl$_{1-4}$

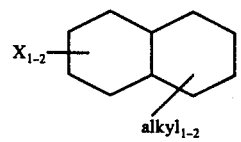

alkyl$_{1-2}$

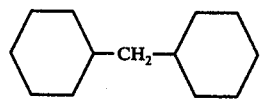

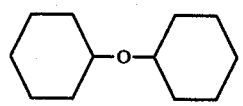

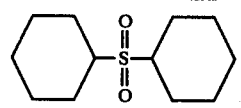

(III) Alkylene ethers

where A is an alkyleneether radical $-A(OA)_n$ where A is alkylene (including cycloalkylene ether radicals) having for example from 2–10 or more carbons such as 2–4, but preferably 2 in each alkylene unit. Typical examples are

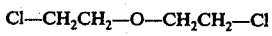

Additional examples of A include groups of the formula $(AO)_n$ where A is

where Y is alkyl, for example

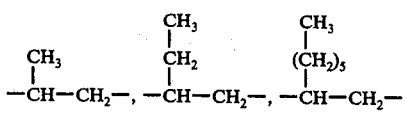

etc.

Thus, A can be methylene, polymethylene, ethylene, propylene, butylene, octylene, etc. In addition $(AO)_n$ may be homo or hetero as to A, to yield for example (ETO)$_a$(PrO)$_b$, (PrO)$_a$(BuO)$_b$, or (PrO—ETO)$_n$; —CH$_2$OCH$_2$CH$_2$OCH$_2$CH$_2$OCH$_2$—etc.

These compounds also include the formal of ethylene chlorohydrin and bromohydrin, for example
ClCH$_2$CH$_2$OCH$_2$OCH$_2$CH$_2$Cl,
ClCH$_2$CH$_2$OCH$_2$CH$_2$OCH$_2$OCH$_2$CH$_2$OCH$_2$CH$_2$Cl
etc. (IV) Unsaturated dihalides

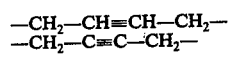

where R$_2$ is an unsaturated aliphatic radical, for example

—CH$_2$—CH=CH—CH$_2$—
—CH$_2$—C≡C—CH$_2$— etc.

Preferred examples of the di-tertiary amines that may be employed in the practice of this invention include:

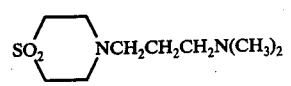

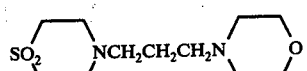

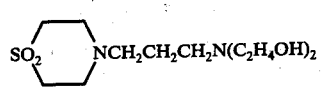

The following examples are used to illustrate the preparation of the polyquaternary polythiazines of this invention.

EXAMPLE 1A 54.0g (0.25 mols) of 1,4-dibromobutane and 55.0g (0.25 mols) of

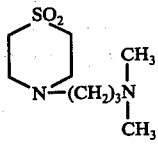

were mixed together, at room temperature, in one liter of an 80:20 mixture, by volume, of Dimethylformamide:water. The reaction mixture was allowed to remain at room temperature (Ca. 23° C) for a period of 300 hours. The polymer was isolated by pouring the solution into a large excess of acetone. The precipitated polymer was filtered; washed quickly with a small amount of solvent, then with benzene and finally with acetone; and dried under high vacuum at 40° C. The resulting polymer had a specific viscosity, in distilled water, of 0.82.

Analysis: Calcd. for polymer -- % Br, 36.65 Found -- % Br, 35.70

The product had the structure,

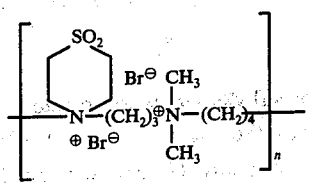

EXAMPLE 2A

In a similar manner 22.0g (0.1 mols) of

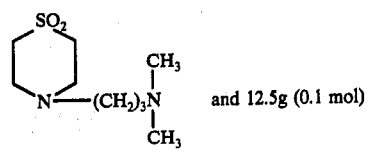 and 12.5g (0.1 mol)

and 12.5g (0.1 mol) of 1,4-dichlorobutene-2 were reacted together at room temperature in 200 ml. of an 80:20 mixture of DMF:H$_2$O. The isolated polymer had a specific viscosity of 0.78 (distilled water).

Analysis: Calcd. —% Cl, 20.55 Found — 19.72

The product had the structure,

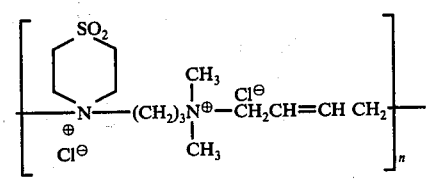

EXAMPLE 3A

In a similar manner 33.0g (0.1 mol) of

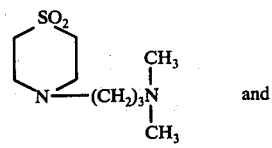 and and 23.0g (0.1 mol) of 1,5-dibromopentane were reacted in 400 ml of DMF:CH$_3$OH (75:25 by volume) at room temperature for 650 hours. The isolated polymer had a specific viscosity, in distilled water, of 1.05. It had the following structure:

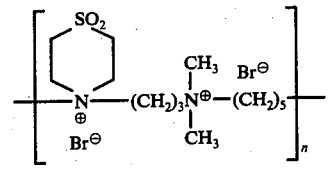

EXAMPLE 4A

In a similar manner 22.0g (0.1 mol) of

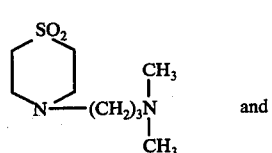 and and 24.0g (0.1 mol) of 1,6-dibromohexane were reacted together in 300 ml. of DMF:H$_2$O (80:20 by volume) at room temperature for 500 hours. The isolated polymer had a specific viscosity of 1.41. It had the following structure:

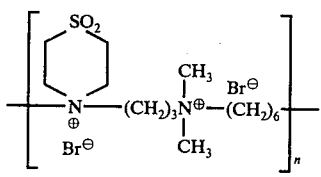

EXAMPLE 5A

In a similar manner 65.5g (0.25 mol) of

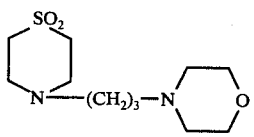

and 54g (0.25 mol) of 1,4-dibromobutane were reacted together at room temp. in 250 ml. of DMF:H$_2$O (80:20 by volume) for a period of 1 month. The isolated polymer had a specific viscosity, in distilled water, of 1.62. It had the following structure:

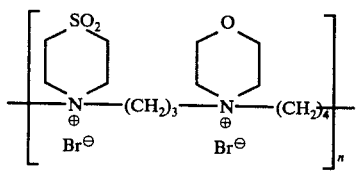

EXAMPLE 6A

In a similar manner 26.2g (0.1 mol) of

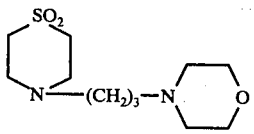

and 12.5g (0.1 mol) of 1,4-dichlorobutene-2 were reacted together at room temp. in 250 ml. of DMF:H$_2$O (80:20 by volume) for a period of 300 hours. The isolated polymer had a specific viscosity, in distilled water, of 1.20. The product had the following structure:

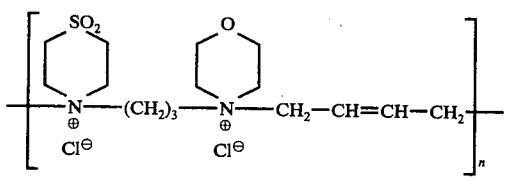

EXAMPLE 7A

In a similar manner 26.2g (0.1 mol) of

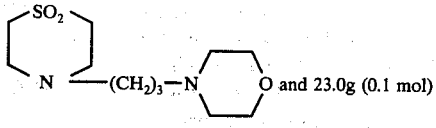

of 1,5-dibromopentane were reacted together at room temp. in 250 ml. of DMF:CH$_3$OH (75:25 by volume) for a period of 360 hrs. The isolated polymer had a specific viscosity, in distilled water, of 0.95. The product had the following structure:

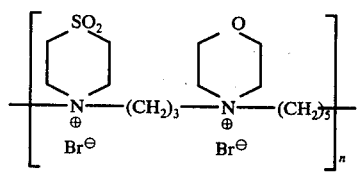

EXAMPLE 8A

In a similar manner 26.2g (0.1 mol) of

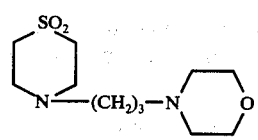

and 24.4g (0.1 mol) of 1,6-dibromohexane were reacted together, at room temp., in 400 ml. of DMF:H$_2$O (80:20 by volume) for a period of 450 hours. The isolated product had a specific viscosity, in distilled water, of 1.20. It had the following structure:

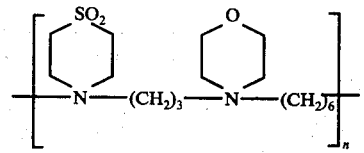

EXAMPLE 9A

In a similar manner 22.0g (0.1 mol) of

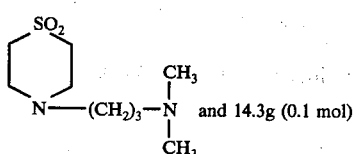

of 1,4-dichloroethylether were reacted together, at room temp., in 100 ml. of DMF:H$_2$O (80:20 by volume) for a period of 1 month. The product had the following structure:

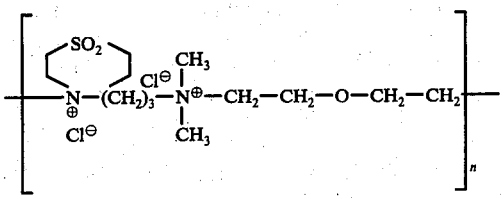

EXAMPLE 10A

In a similar manner 22.0g (0.1 mol) of

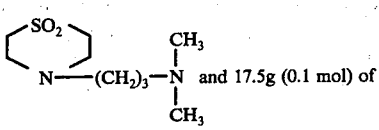 and 17.5g (0.1 mol) of p-xylene dichloride were reacted together at room temp. in 100 ml. of DMF:H$_2$O (80:20 by volume) for a period of 1 month. The product had the structure:

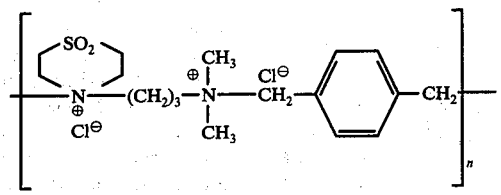

EXAMPLE 11A

In a similar manner 22.0g (0.1 mol) of

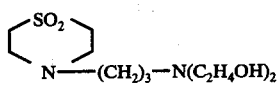

and 21.6g (0.1 mol) of 1,4-dibromobutane were reacted together, at room temp., in 250 ml. of DMF:H$_2$O (80:20 by volume) for a period of 300 hrs. The product had a specific viscosity of 0.89. The polymer had the following structure:

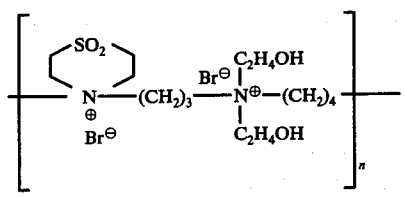

USE AS FLOCCULATING AGENTS

Water Clarification

The present invention relates to a method for the clarification of water containing suspended matter.

According to the present invention clarification of water containing suspended particles of matter is effected by adding to such water the polymers of this invention.

Water containing suspended particles which may be treated by the present invention may have its origin either in natural or artificial sources, including industrial and sanitary sources. Waters containing suspended particles of natural origin are usually surface waters, wherein the particles are suspended soil particles (silt), although subsurface waters may also be treated according to the present invention. Water having its origin in industural process (including sanitary water) operations may contain many different varieties of suspended particles. These particles are generally the result of the particular industrial or sanitary operation concerned. Prior to discharging such industrial waste waters into natural water courses it generally is desired that the suspended matter be removed.

The present process may likewise be applied to water contained in stock or fish ponds, lakes or other natural or artificial bodies of water containing suspended solids. It may be applied to industrial water supplied either in preparation therefor, during or after use and prior to disposal. It may be applied to sanitary water supplies either for the elimination of suspended solids prior to use for such purposes, or it may be applied to such waters which have become contaminated with impurities from any source.

Most naturally occurring waters contain an amount of simple electrolytes (sodium, potassium, ammonium, calcium, aluminum salts, etc.) in excess of that necessary for the initial aggregation of the ultimate silt particles.

This is likewise true of particles of suspended material in industrial or sanitary waters. The ultimate particles of silt or other materials are therefore naturally somewhat aggregated by reason of the presence of such electrolytes. However, the forces binding such ultimate particles together are not great and moreover are not such as to generally effect either rapid settling rates of the flocculated material or strong enough to prevent deflocculation.

The compositions of the invention cause rapid flocculation and also reinforced the formed aggregates of particles causing a general tightening or bonding together of the initial particles and an increased rate of coagulation and settling, thus forming a less turbid supernatant liquid.

The addition of the compositions of the invention to the water suspension should be made in such a fashion that the resulting flocculation and aggregation of the particles takes place uniformly throughout the body of water. In order to obtain a uniform addition of the compositions of the invention to the water-borne suspension it is generally desirable to prepare a relatively dilute stock solution of the inventive compositions and then to add such solution to the body of water in the proportions indicated above. Clarification may take place either in the natural body of water or it may be caused to take place in hydraulic thickeners of known design.

The amount of inventive compositions to be employed will vary depending upon the amount of the degree of subdivision of the solids to be agglomerated or flucculated, the chemical nature of such solid and the particular inventive compositions employed. In general, I employ at least a sufficient amount of the inventive compositions to promote flocculation. In general, I employ about 0.5–10,000 ppm or more, such as about 1–5,000 ppm, for example about 2–500 pm, but preferably about 5–25 ppm. Since the economics of these processes are important, no more than the minimum amount required for efficient removal is generaly employed. It is desired, of course, to employ sufficient of the inventive compositions so flocculation will take place without causing the formation of stable dispersions.

The precipitating action of the inventive compositions can be employed in the application of loading or filling materials to textiles or paper in order to obtain special effects. As an example, rosin size is often added to paper pulp prior to the formation of the sheet and precipitated in the aqueous pulp by aluminum sulfate (papermakers' alum). While admirably serving this purpose it is recognized that aluminum sulfate is objectionable not only because of its actual corrosiveness upon metals but also because of its hardening effect on organic substances such as cellulose. (II) Water By adding the inventive compositions to the paper machine beater, either prior to or after the addition of size of filler, complete precipitation can be achieved without the use of alum. The resulting paper is obtained thus substantially free of electrolytes and the white water is clear and free of suspended particles. In this connection a difficulty often encountered with alum when applying certain colors to paper, which difficulty is manifested by weakening of the color, is also avoided.

In the processing of fine mineral particles in aqueous suspension the inventive composition flocculating agents will be especially useful. In the processing of ores to separate valuable mineral constituents from undesirable matrix constituents, it is frequent practice to grind the ore into a finely-divided state to facilitate separation steps such as selective flotation and the like. In many ore dressing procedures, the finely-divided ore is suspended in water to form a pulp or slime. After processing, it is usually desirable to dewater the pulps or slimes either by sedimentation or filtering. In such operations, certain ores are particularly troublesome in that the finely-divided ore, when suspended in water, forms a stable slime which settles very slowly, if at all. Such slimes are unsuitable for concentration or dewatering by sedimentation and are difficult to dewater by filtration because of the tendency to clog the pores of the filter, thus leading to excessively time-consuming and inefficient operation of the filters. In some cases, for example, in certain phosphate mining operations, the formation of very stable suspensions of finely-divided mineral results not only in the loss of considerable valuable mineral as waste but also requires large expenditures for the maintenance of holding ponds for the waste. Similar problems are involved in processing gold, copper, nickel, lead, zinc, iron, such as taconite ores, uranium and other ores, and the inventive flocculating agents will be useful in these operations.

Some specific additional applications for the flocculating agent for the invention, not intended to be limiting but merely illustrative are listed below. The inventive composition can be used for the clarification of beers or wines during manufacture. Another use is in processing effluents in pharmaceutical operations for the recovery of valuable products or removal of undesirable by-products. A particularly important use for these flocculating agents is in the clarification of both beet sugar and can sugar juices in their processing. Still another use is for flocculation and recovery of pigments from aqueous suspensions thereof. The inventive composition will be particularly useful in sewage treatment operations as a flocculation agent. A further use is to promote by flocculation the removal of coal from aqueous suspensions thereof. In other words the inventive composition flocculating agents of the invention are generally useful for processing aqueous effluents of all types to facilitate the removal of suspended solids.

A water soluble or water disposable composition, to the extent of effective concentration, is employed.

These compositions can also be employed in the process of flocculating white water and/or recycling of the precipitate solids in the paper making process described in U.S. application Ser. No. 347,023 filed Feb. 24, 1964, now abandoned and other processes described therein.

The following examples are presented by way of illustration and not limitation.

FLOCCULATION EXAMPLE A

Into 500 ml. of a 5% brine solution containing 25 ppm of FeS was introduced a solution containing 2 ppm of the polyquaternary polythiazine polymer (Example 1A). The solution was stirred for 1 minute at 100 r.p.m. on a Phipp and Bird "Floc Stirrer" apparatus. The speed was then reduced to 20-35 r.p.m. for 10 minutes, and then stopped. The floc size and precipitation rate of the floc were excellent. The water color after precipitation was also excellent.

FLOCCULATION EXAMPLE B

To an aqueous suspension of 300 ppm bentonite (Volclay, 625 mesh, American Colloid) was added a solution of the polyquaternary polythiazine described in Example 5A. The polymer dosage was 10 ppm. The solution was stirred for 1 minute at 100 r.p.m. on a "Phipp and Bird" floc stirrer apparatus. The speed was then reduced to 20-35 r.p.m. for 10 minutes, and then stopped. The supernatant liquid was drawn off and analyzed for residual turbidity. The turbidity was 15% of that of the untreated water which also contained 300 ppm of bentonite.

Polymers of the present invention can be employed as flocculating agents in the following industries:
(1) Petroleum industry
(2) Food industry such as in the dairy industry, the canning, freezing and dehydration industries
(3) Metal plating industry
(4) Chemical and pharmaceutical industries
(5) Mining industry, for example, in the phosphate mining industry such as in phosphates slimes.
(6) Fermentation industries, such as in alcohol, beer, yeast, antibiotics, etc. production
(7) Tanning industry
(8) Meat packing and slaughter house industry
(9) Textile industry
(10) Sugar refining industry
(11) Coal industry
(12) Soap industry
(13) Sewage purification
(14) Corn starch industry
(15) Fat processing and soap industry
(16) Paper industry

USE AS A DEMULSIFIER

Most naturally occurring emulsions of petroleum oil and water take the form of a water-in-oil emulsion in which the oil is the continuous phase and tiny droplets of water are dispersed in the oil. Oftentimes, however, reversed emulsions are encountered either in the production, handling or refining of petroleum oil. Reversed emulsions are of a character quite different from the usual water-in-oil emulsions and must be treated in a different manner with different chemicals in order to resolve the reversed emulsion into oil and water phases.

In general, I employ 0.5–10,000 ppm or more, such as 1–5,000 ppm, for example about 2–500 ppm, but preferably 5–50 ppm.

The invention is illustrated by the following example.

Demulsification Example A

An oil-in-water emulsion was prepared by mixing 25g. of a non-detergent motor oil with 200g. of water in a Waring Blender set at high speed. Mixing time was 15 minutes. The resulting product was placed in a separatory funnel and allowed to stand overnight. About three fourths of the lower phase, a very hazy appearing emulsion of oil-in-water was removed from the funnel and recovered. Four batches of the emulsion were prepared and combined. Each of five 100 ml. graduated cylinders was filled to the 100 ml. mark with the emulsion. The first cylinder was set aside as a control while the emulsion in each of the other graduated cylinders was treated with a predetermined quantity of demulsifier. All runs were made at 25° C.

The following table shows the test conditions and results of these tests.

Table 1

| Cylinder Number | Demulsifier (ppm) | Appearance after 24 hrs. |
|---|---|---|
| 1 | none (control) | Very hazy |
| 2 | Ex. 1A(25) | Clear |
| 3 | Ex. 3A(25) | Clear |
| 4 | Ex. 5A(25) | Clear |
| 5 | Ex. 6A(25) | Clear |

USE AS A MICROBIOCIDE

(I) In Water Treatment

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algai, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bacterial, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae, and all forms of microbial life therein.

(II) A Water Flooding in Secondary Recovery of Oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20–30 percent of the oil in a producing formation that is usually recovered in the primary process. In flooding operation, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Free-plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

(III) Hydrocarbon Treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

MICROBIOCIDAL TESTING

The screening procedure was as follows: a one percent by weight solution of the test compound in water was prepared. The solution was aseptically added to a sterile broth that would support the growth of the test organism, *Desulfovibro desulfuricans*, to provide a concentration of 50 and 100 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 25 hours. The absence or presence of growth of the microoganisms was determined by visual inspection by an experienced observer.

Following is a summary of the results of the testing of examples of this invention.

| Compound Example | Concentration of test compound, ppm | Results |
| --- | --- | --- |
| 2A | 50 | Gave control.[1] |
| 3A | 40 | " |
| 5A | 40 | " |

[1]By control is meant that the test compound was biostatic or biocidal--i.e., no growth of the test organism occurred under the test conditions.

USE AS ALGICIDES

This invention relates to the use of the product polyquaternary ammonium compounds in controlling the growth of algae. More particularly, the foregoing product is useful as an algicide in industrial and other systems employing water as a major component.

The growth of algae in systems as defined above has a deleterious effect upon the efficient operation of such systems if means are not taken to inhibit the growth of said algae.

It has been suggested in the chemical literature that certain quaternary ammonium compounds could be used as algicides. These compounds while effective as algicides are not entirely satisfactory. Quaternary ammonium compounds are cationic surfactants and when added to water even in minute quantities, produce a system tending to foam, an objectionable result in most applications. Another objection to the use of these quaternary compounds is that they are generally very irritating to the skin of warmblooded animals.

It is, therefore, a principal object of the present invention to provide a process for the control of algae which process obviates the disadvantages of the prior art processes of this type.

The use of the polyquaternary ammonium compounds of this invention as algicides is illustrated by the following example.

The compounds were tested for algicidal activity, using the "Standard Tube Dilution Test," which is common knowledge to those skilled in the art. This test utilizes a suitable nutrient broth which is treated to provide various concentrations of the antimicrobial candidates of this invention.

To the sterile broth contained in test tubes at 9 ml. volume was added 1.0 ml. of a dilution of test antimicrobial solution, at levels, of 1,000, 500, 250, 100, 50, 10 and 5 parts per million respectively. Following this, each tube was inoculated with 0.1 ml. of a broth suspension of a 24 hour culture of 30,000 cells per ml. of algae.

The tubes so inoculated were incubated at 28° C. for 7 days for algae. Following the aforementioned incubation periods, the tubes were examined for the presence or absence of macroscopic growth. The lowest concentration of test material not permitting macroscopic growth is designated as the minimum inhibitory level. The test organisms employed were *Penicillin exponsum* = P.e.; and *chlorella pyranoidosa* = C.p.

Table 2

| Example | Parts per million of product inhibiting: Algae | |
| --- | --- | --- |
|  | P.e. | C.p. |
| 2A | 50 | 10 |
| 3A | 100 | 10 |
| 5A | 50 | 10 |
| 6A | 50 | 10 |

CORROSION INHIBITION

This invention also relates to the inhibition of corrosion, particularly the corrosion of metals in contact with the acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results with be experienced. There has been a continuing search for corrosion inhibitors which can be used effectively in small concentrations, and which are economical to produce. The need is also for corrosion inhibitors which are effective at high temperatures, e.g., 200° F. and above, such as are found in operations involving acidic solutions, particularly oil-well acidizing where higher and higher temperatures are found as the well extends further into the earth.

While the compounds of this invention are of themselves particularly good acid corrosion inhibitors, optionally they may be blended with acetylenic alcohols, dispersing and solubilizing agents such as ethoxylated phenols, alcohols, and fatty acids. They may also be blended with such known acid inhibitors as the quinoline or alkyl pyridine quaternary compounds or synergists such as terpene alcohols, formamide, formic acid, alkyl amine, alkylene polyamines, heterocyclic amines, and the like.

Quaternary ammonium compounds may be illustrated by C-alkyl pyridine-N-methyl chloride quaternary, C-alkyl pyridine-N-benzyl chloride quanternary, quinoline-N-benzyl chloride quaternary, isoquinoline-N-benzyl chloride quaternary, thioalkyl pyridine quaternaries, thioquinoline quaternaries, benzoquinoline quaternaries, thiobenzoquinoline quaternaries, imidazole quaternaries, pyrimidine quaternaries, carbazole quaternaries, the corresponding ammonium compounds, pyridines and quinolines may also be used alone or in combination with the quaternary compounds. Thus a pyridine plus quinoline quaternary, a quinoline plus quinoline quaternary, or quinoline or amine alone or in combination may be used.

The formic acid compound may be selected from the esters and amides of formic acid. The formic acid compound may be from the group consising of formate esters of the structure:

HCOOR where R is a monoaryl group, an alkyl group having 1 to 6 carbon atoms, cyclo-alkyl residues having 5 to 6 carbon atoms, alkenyl and alkynl groups having 2 to 6 carbon atoms which may contain functional groupings selected from —C—OH, —OH, =C=O, —COH, —SH, and NH$_2$, Examples of the formic acid compound are: methyl formate, ethylformate, benzyl formate, other alkyl and aryl formates, and the like. Other examples include formamide, dimethyl formamide, formanilide, and the like. Mixtures of the esters and mixtures of the amides may be used.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareousmagnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

Corrosion Test Procedure

In these tests the acid solutions were mixed by diluting concentrated hydrochloric acid with water to the desired concentrations.

Corrosion coupons of N-80 steel (ASTM) were pickled in an uninhibited 10% HCl solution for 10 minutes, neutralized in a 10% solution of NaHCO$_3$, dipped in acetone to remove water and allowed to dry. They were then weighed to the nearest milligram and stored in a desicator.

In most of the test, a 25cc/in$^2$ acid volume to coupon surface area ratio was used. After the desired amount of acid was poured into glass bottles, the inhibitor was added. The inhibited acid solution was then placed in a water bath which had been set at a predetermined temperature and allowed to preheat for 20 minutes. After which time, the coupons were placed in the preheated inhibited acid solutions. The coupons were left in the acid solutions for the specified test time, then removed, neutralized, recleaned, rinsed, dipped in acetone, allowed to dry, then reweighed.

The loss in weight in grams was multiplied times a calculated factor to convert the loss in weight to lbs./ft$^2$/24 hrs. The factor was calculated as follows:

$$\frac{\frac{144 \text{ in}^2}{\text{ft}^2}}{\frac{454 \text{ g}}{\text{lb}} \times \text{Surface Area of Coupon (in}^2\text{)} \times \frac{1 \text{ day}}{24 \text{ hrs}}} = \text{Factor}$$

All tests were carried out under the following conditions.

| (1) Concentration 3000 ppm | (4) 15% HCl |
|---|---|
| (2) Test Temp. 150° F | (5) Employing N-80 |
| (3) Time 4 hours | corrosion coupon |

The results of these tests are included below:

| Inhibitor | Corrosion rate (lbs./ft$^2$/day) |
|---|---|
| Ex. 1A | 0.048 |
| Ex. 2A | 0.063 |
| Ex. 3A | 0.075 |
| Ex. 4A | 0.084 |
| Ex. 5A | 0.052 |
| Ex. 6A | 0.063 |
| Ex. 7A | 0.072 |
| Ex. 8A | 0.071 |
| Ex. 11A | 0.051 |
| Blank | 2.32 |

Applications in which the inhibitors of the present invention are particularly useful include oil-well acidizing solutions, metal pickling, cleaning and polishing baths, boiler cleaning compositions and the like.

USE AS ANTI-STATIC AGENTS

It is well known that synthetic linear polymer textile material, e.g., polyamide textile material, is liable to become adventitious friction in the course of use, for example, friction arising from movements on the part of the wearer of the textile material concerned. Materials such as nylon, rayon and dacron are notorious examples.

To demonstrate the effectiveness of the polyquaternary compounds of this invention as anti-static agents, the following example is cited.

Anti-static Properties. A sample of dacron cloth was immersed in a DMF:MeOH (1:4 by volume) solution of the polyquaternary ammonium compound described in Example 3A (5g./100 ml) for 6 hours and dried in vacuum overnight at 30° C.

The dry specimens were subjected to friction by means of a teflon sheet (known to induce a positive potential) and wool (known to induce a negative potential). In Table 3, the voltages of a polymer treated sample is compared with an untreated sample.

Table 3

| | Results of Static Electrification Tests Electrostatic Potential (Volts) | |
|---|---|---|
| *Fabric | Charging with Teflon | Charging with Wool |
| Untreated dacron | +20,000 | −20,000 |
| Treated dacron | 0 | 0 |

*Size of sample 6" × 6'

The tests were carried out by means of a static meter model CMI-7777 in a relative humidity of 20%.

USE IN THE FORMATION OF POLYELECTROLYTE COMPLEXES

In 1961 Michales and Miekka, J. Phys. Chem., 65, 1765, reported that the interaction of aqueous solutions of high molecular weight poly(styrene sodium sulfonate) with aqueous solutions of poly(vinylbenzyltrimethylammonium) chloride leads to an insoluble precipitate, the most likely structure of which consists of a cross-linked polymer. The cross-linking is due to the interaction between the negative sulfonate anion and the positive ammonium cation. This type of polyelectrolyte complex, or polysalt, may be free from sodium chloride, since the latter diffuses out from the polymeric matrix in the presence of water.

Soluble polymers are used in the synthesis of the complexes, which may be obtained in neutral form or with an excess of either positively or negatively charged groups and solvent systems have been developed from which the polysalt may be cast to form a variety of membranes of commercial interest. Some properties of Polyion complexes are:

1. Insolubility in common solvents
2. Dielectric properties very sensitive to moisture and ion content
3. High Ic conductance in contact with aqueous electrolytes
4. Permeable to electrolytes
5. Impermeable to macrosolutes
6. Rubbery when wet, hard and brittle when dry.

Some possible applications of Polyelectrolytes complexes are:

1. Ultrafiltration membranes
2. Battery separators
3. Plastic composites
4. Electrically conductive and anti-static coatings
5. Medical and surgical prosthetic materials.

To illustrate the effectiveness of the polyquaternary ammonium compounds of this invention in forming complexes with high molecular anionic polymers, the following example is cited.

Complex Example A

A dilute (3%) aqueous solution of the polyquaternary polythiazine described in Example 1A was mixed with a dilute (3%) aqueous solution of a commercial poly(styrene sodium sulfonate) resin. An insoluble precipitate was immediately formed. The precipitated solid was filtered and washed six times with large quantities of water. The solid was dried in vacuum at 40° C for 24 hrs. The product was a hard brittle solid that was insoluble in common organic solids. It was useful as a plastic composite.

I claim:

1. Polymers of quaternary thiazines having following recurrent structure

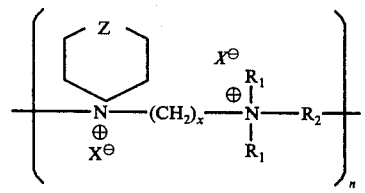

where Z is S, SO, $SO_2$, x is 2 or more, $R_1$ is alkyl or hydroxyalkyl or both $R_1$'s may be joined to form a heterocyclic group, $R_2$ is alkylene, alkenylene, aralkylene, or alkylene ether, X is a halide and n is a number fron 3-500.

2. The polymer of claim 1 where Z is $SO_2$.
3. The polymer of claim 1 where x is 2-10.
4. The polymer of claim 3 where Z is $SO_2$.
5. The polymer of claim 1 where $R_1$ is alkyl.
6. The polymer of claim 5 where Z is $SO_2$.
7. The polymer of claim 1 wherein the $R_1$'s are joined to form with the nitrogen an

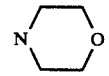

group.

8. The polymer of claim 7 where Z is $SO_2$.
9. The polymer of claim 1 where $R_2$ is alkylene.
10. The polymer of claim 1 where X is chloride.
11. The polymer of claim 1 wherein n is 3-100.
12. The process of inhibiting corrosion in acidic systems which comprises treating said system with the polymer of claim 1.
13. The process of inhibiting microbiological growth in aqueous systems which comprises treating said system with the polymer of claim 1.
14. The process of water clarification which comprises treating an aqueous system with the polymer of claim 1.
15. The process of demulsification which comprises treating an emulsion with the polymer of claim 1.
16. Textile material containing an anti-static amount of the polymer of claim 1.
17. The reaction product of the polymers of claim 1 with a polystyrene sulfonate.

* * * * *